(12) United States Patent
Bnayahu et al.

(10) Patent No.: US 8,819,037 B2
(45) Date of Patent: Aug. 26, 2014

(54) SEARCH OPTIMIZATION IN A COMPUTING ENVIRONMENT

(71) Applicant: International Business Machines Corporation, Armonk, NY (US)

(72) Inventors: Jonathan Bnayahu, Haifa (IL); Ariel Landau, Nesher (IL); Mordechai Nisenson, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/674,061

(22) Filed: Nov. 11, 2012

(65) Prior Publication Data
US 2013/0066825 A1  Mar. 14, 2013

Related U.S. Application Data

(63) Continuation of application No. 13/179,582, filed on Jul. 11, 2011.

(51) Int. Cl.
*G06F 17/30* (2006.01)
*G06F 17/00* (2006.01)

(52) U.S. Cl.
CPC ................................ *G06F 17/30569* (2013.01)
USPC ............................ 707/756; 707/758; 706/57

(58) Field of Classification Search
CPC .................................................. G06F 17/30569
USPC ................................ 707/756, 999.01; 706/57
See application file for complete search history.

(56) References Cited

U.S. PATENT DOCUMENTS

| | | | |
|---|---|---|---|
| 5,214,704 A * | 5/1993 | Mittenthal | 380/37 |
| 5,301,104 A * | 4/1994 | Yalamanchili | 712/12 |
| 5,963,565 A | 10/1999 | Rezvani et al. | |
| 6,678,868 B2 * | 1/2004 | Lam | 716/55 |
| 6,694,306 B1 * | 2/2004 | Nishizawa et al. | 707/714 |
| 6,747,580 B1 * | 6/2004 | Schmidt | 341/50 |
| 7,277,438 B2 | 10/2007 | Ambe et al. | |
| 7,315,936 B2 * | 1/2008 | Koch, III | 712/223 |
| 7,519,952 B2 | 4/2009 | Bordawekar et al. | |
| 7,603,647 B2 | 10/2009 | Gilford et al. | |
| 7,805,387 B2 * | 9/2010 | Lalvani | 706/13 |
| 8,526,482 B2 * | 9/2013 | Dent | 375/135 |
| 2004/0100959 A1 | 5/2004 | Relan | |
| 2005/0027542 A1 | 2/2005 | Bordawekar et al. | |
| 2008/0016099 A1 | 1/2008 | Ikeda | |
| 2008/0059841 A1 | 3/2008 | Bordawekar et al. | |
| 2009/0248648 A1 * | 10/2009 | Johnson et al. | 707/4 |
| 2010/0002483 A1 | 1/2010 | Gronlund | |
| 2010/0082654 A1 | 4/2010 | Zhang et al. | |
| 2010/0174893 A1 | 7/2010 | Rivera | |

\* cited by examiner

*Primary Examiner* — Miranda Le

(57) ABSTRACT

Systems and methods for verifying membership in one or more sets that are subsets of a global set are provided. The method compromises representing members of the global set by mapping each member to a distinct Boolean variable of length d, wherein $2^d$ is not less than the number of members in the global set; representing each of the given subsets of the global set by a Boolean expression which evaluates to a first value for any of the assignments to the Boolean variables which represent members of the subset, and which evaluates to a second value for any of the assignments to the Boolean variables which represent members of the global set that are not members of the subset.

6 Claims, 10 Drawing Sheets

- Codes:
  - 1, 2, 3, 4, 5, 6, 7, 8
- Sets:
  - A = {1,2,6}
  - B = {1,3,6}
  - C = {2,3,5,6,7}
  - D = {1,4,6,7,8}
  - E = {4,5,8}
  - F = {3,5,7}

- Co-occurrence counts (could be used by mapping algorithm)
  - <1,2> = 1         <1,6> = 3
  - <2,6> = 2         <3,6> = 2
  - <2,3> = 1         <2,5> = 1
  - <2,7> = 1         <3,5> = 2
  - <3,7> = 2         <5,6> = 1
  - <5,7> = 2         <4,6> = 1
  - <4,7> = 1         <4,8> = 2
  - <4,5> = 1         <1,4> = 1
  - <1,7> = 1         <1,8> = 1
- Therefore it would be useful if <1,6>, <2,6>, <3,6>, <3,5>, <3,7>, <5,7>, <4,8> would be neighbors

*FIG. 1*

- Mapping:
  - 1 = 001
  - 2 = 010
  - 3 = 100
  - 4 = 011
  - 5 = 110
  - 6 = 000
  - 7 = 101
  - 8 = 111

Set A = {1,2,6}

- Mapping:
  - *1 = 001*
  - *2 = 010*
  - *3 = 100*
  - *4 = 011*
  - *5 = 110*
  - *6 = 000*
  - *7 = 101*
  - *8 = 111*
- A = 0*0 or 00*

Set B = {1,3,6}

- Mapping:
  - *1 = 001*
  - *2 = 010*
  - *3 = 100*
  - *4 = 011*
  - *5 = 110*
  - *6 = 000*
  - *7 = 101*
  - *8 = 111*
- B = *00 or 00*

Set C = {2,3,5,6,7}

- Mapping:
  - 1 = 001
  - 2 = *010*
  - 3 = *100*
  - 4 = 011
  - 5 = *110*
  - 6 = *000*
  - 7 = *101*
  - 8 = 111
- C = **0 or 10*

Set D = {1,4,6,7,8}

- Mapping:
  - *1 = 001*
  - *2 = 010*
  - *3 = 100*
  - *4 = 011*
  - *5 = 110*
  - *6 = 000*
  - *7 = 101*
  - *8 = 111*
- D = **1 or 00*

Set E = {4,5,8}

- Mapping:
  - 1 = 001
  - 2 = 010
  - 3 = 100
  - *4 = 011*
  - *5 = 110*
  - 6 = 000
  - 7 = 101
  - *8 = 111*
- E = 11* or *11

Set F = {3,5,7}

- Mapping:
  - 1 = 001
  - 2 = 010
  - *3 = 100*
  - 4 = 011
  - *5 = 110*
  - 6 = 000
  - *7 = 101*
  - 8 = 111
- F = 1*0 or 10*

SEARCH OPTIMIZATION IN A COMPUTING ENVIRONMENT

CROSS-REFERENCE TO RELATED APPLICATION

This application is a divisional application of U.S. patent application Ser. No. 13/179,582 entitled, "SEARCH OPTIMIZATION IN A COMPUTING ENVIRONMENT", filed on Jul. 7, 2011 and is assigned to the same assignee in the present application, contents of which are incorporated by reference herein in its entirety.

COPYRIGHT & TRADEMARK NOTICES

A portion of the disclosure of this patent document may contain material, which is subject to copyright protection. The owner has no objection to the facsimile reproduction by any one of the patent document or the patent disclosure, as it appears in the Patent and Trademark Office patent file or records, but otherwise reserves all copyrights whatsoever.

Certain marks referenced herein may be common law or registered trademarks of the applicant, the assignee or third parties affiliated or unaffiliated with the applicant or the assignee. Use of these marks is for providing an enabling disclosure by way of example and shall not be construed to exclusively limit the scope of the disclosed subject matter to material associated with such marks.

TECHNICAL FIELD

The disclosed subject matter relates generally to search optimization in a computing environment.

BACKGROUND

In insurance claim processing, there is a need to define different claim handling processes for different codes used for medical procedures or drug prescriptions. One of the most widely used coding systems is the "International Statistical Classification of Diseases and Related Health Problems" (ICD) published by the World Health Organization. ICD provides codes to classify diseases and a wide variety of signs, symptoms, abnormal findings, complaints, social circumstances, and external causes of injury or disease. Under this system, every health condition can be assigned to a unique category and given a code. Such categories can include a set of similar diseases.

The use of ICD codes is mandated by law in many countries. In the United States, for example, ICD's 9th revision (ICD-9) has been the mandated coding standard for health insurance claims, including Medicare claims, since 1988. In the currently used claim processing methods, the codes are often stored in tables or groups. The number of tables is in the order of tens of thousands. The number of codes covered by each table varies and can be in the order of thousands. If the codes for a group of related procedures or diagnosis are sequential, the tables may be implemented to group the codes in predefined ranges. Setting a range as defined by a table saves computation time during a search, because it reduces the sizes of the tables (allowing more tables and their contents to be stored in memory and CPU caches) and because fewer operations are necessary to search a smaller table.

Due to the nature of the codes in the ICD-9 code sets, the above approach has been mostly useful for processing related claims. However, ICD-9 is to be replaced with the ICD-10 code sets effective Oct. 1, 2013. Industry experts expect that the above-noted grouping approach may be unsuitable for ICD-10 because the code implementation in ICD-10 is scattered in a way that use of ranges may result in creating large code tables that are inefficient for the purpose of searching. Certain methods, such as entry compression, encoding or clustering are available that may help reduce the size of the tables. Such solutions, never-the-less, result in an increase in search time.

SUMMARY

For purposes of summarizing, certain aspects, advantages, and novel features have been described herein. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested herein.

In accordance with one embodiment, systems and methods for verifying membership in one or more sets that are subsets of a global set are provided. The method compromises representing members of the global set by mapping each member to a distinct Boolean variable of length d, wherein $2^d$ is not less than the number of members in the global set; representing a subset of the global set by a Boolean expression which evaluates to a first value for any of the assignments to the Boolean variables which represent members of the subset, and which evaluates to a second value for any of the assignments to the Boolean variables which represent members of the global set that are not members of the subset.

In accordance with one or more embodiments, a system comprising one or more logic units is provided. The one or more logic units are configured to perform the functions and operations associated with the above-disclosed methods. In yet another embodiment, a computer program product comprising a computer readable storage medium having a computer readable program is provided. The computer readable program when executed on a computer causes the computer to perform the functions and operations associated with the above-disclosed methods.

One or more of the above-disclosed embodiments in addition to certain alternatives are provided in further detail below with reference to the attached figures. The disclosed subject matter is not, however, limited to any particular embodiment disclosed.

BRIEF DESCRIPTION OF THE DRAWINGS

The disclosed embodiments may be better understood by referring to the figures in the attached drawings, as provided below.

FIG. 1 illustrates an exemplary global code set and several code subset in accordance with one or more embodiments.

Features, elements, and aspects that are referenced by the same numerals in different figures represent the same, equivalent, or similar features, elements, or aspects, in accordance with one or more embodiments.

DETAILED DESCRIPTION OF EXAMPLE EMBODIMENTS

Figure 2:
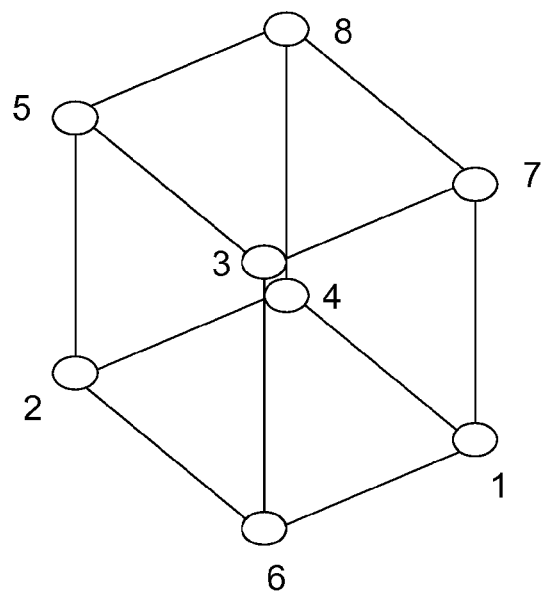
FIG. 2 is an exemplary diagram of a method of mapping the codes in the global code set shown in FIG. 1 into a multi-dimensional data structure, in accordance with one embodiment.

In the following, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others.

In accordance with one embodiment, systems and methods are provided for arranging codes into multiple code sets in a multi-dimensional space, where a range that defines a code set is represented by a cross-section in the multi-dimensional space. It is noted that depending on implementation the code sets may cross-over (i.e., a first code set may include one or more codes common to a second code set).

In one embodiment, a global code set is mapped into a multi-dimensional structure, such as a hypercube, for example. In such example embodiment, a code in the global code set may be represented by a vertex in a d-dimensional data structure (hereafter referred to as a hypercube by way of example and for the purpose of brevity), where "d" represents the number of vertices in the hypercube. A subset of the global code set may be represented as a cross-section (e.g., a hyper-rectangle) of the d-dimensional hypercube.

To determine whether a target code belongs to a code set in the multi-dimensional space, a method is implemented to detect whether a target code belongs to one of the several subsets of the global code set. In the above example embodiment, this is accomplished by determining if a vertex that represents the target code is in a cross-section of the d-dimensional hypercube. As provided in further detail below, the above problem may be solved as an intersection problem on d literals that are assigned Boolean values.

It is noteworthy that while calculations, equations and solutions provided in this disclosure are represented in Boolean or binary values corresponding to bits or strings of 0s and 1s, other encodings that accomplish the same results may be used. Therefore, the scope of the claimed subject matter should not be construed as limited to the particular Boolean values or embodiments that use such details and values, where other implementations are also possible to achieve the same or a similar objective.

Referring to FIGS. 1, 2 and 3A to 3F, an exemplary embodiment is illustrated in which a global code set includes codes 1 through 8, with a grouping of the codes into six sets represented as sets A through F (see FIG. 1, left column). Please note that the values and the sequencing of the codes in the global code set provided here are exemplary. The code values may be numeric, text, or of any other type and in any sequence. For example, the global code set may include {apple, orange, red, blue, green, tiger, ABCDE, 30} as values for codes 1 through 8.

For the purpose of simplicity, in the following, we discuss one or more embodiments with reference to the example values provided in the figures. It should be noted, however, that the details and the values are exemplary and are not to be construed as limiting the scope of the claimed subject matter to the specifics. Further, in the simplified examples shown in the figures, certain codes in the global set may be associated with one another based on one or more relationships. As such, some of the codes may be deemed as co-occurring (see FIG. 1, right column).

It is noteworthy that co-occurrences of a pair of codes, for example, may be determined for codes in given tables in advance based on a co-occurrence count. In FIG. 1, for example, the pair <1,6> has a count equal to 3, which is a count that is higher than any other pair. The counts are useful for creating an effective mapping between the codes and the vertices of the hypercube so that the codes with the highest rate of co-occurrence are grouped in neighboring vertices of the hypercube, where possible.

Depending on implementation, if the rate or level of co-occurrence of two or more codes can be determined in advance, then those codes with the highest level of co-occurrence may be designated as forming a neighborhood of vertices in the d-dimensional hypercube, where the vertices are close to each other in terms of distance in the d-dimensional hypercube. For example, four vertices that represent co-occurring codes may be grouped to form a square in the hypercube. Such arrangement would help optimize the grouping of the codes that enjoy a higher level of co-occurrence into a cross-section of the d-dimensional hypercube.

Referring to FIG. 2, depending on implementation, one or more codes in the global code set may be mapped into the vertices of a d-dimensional hypercube. In FIG. 2, a 3-dimensional hypercube having $2^3$ vertices is illustrated with a one-to-one mapping of the 8 codes in the global set to each of the vertices in the 3-dimensional hypercube. As shown, the mapping to the vertices may be represented based on a binary code of length 3. (Please note that in this simplified example, the value of the binary code is incidentally equal to the decimal value of the corresponding code. This is, however, is not a necessary implementation. As noted earlier, the value of each code can be anything else and is not dependent on the binary mapping values provided by way of this example).

One skilled in the art would appreciate that in a scenario with a larger number of members in the global set, a larger scale multi-dimensional hypercube will be utilized. Depending on implementation, to have enough vertices to map to all the codes in the global code set, the dimension d for the hypercube would satisfy the following equation: $d >= \log_2 n$, where n is the total number of codes in the global set.

As illustrated in the example of FIG. 2, a Boolean value having three literals is assigned to each code in the global set, such that said Boolean value maps to a vertex in the d-dimensional hypercube. For example, code 1 is represented by Boolean literals '001' which is mapped to vertex 1, code 2 is represented by Boolean literals '010' which is mapped to vertex 2, and so on. In this example, d is equal to 3 and thus the 3-dimensional hypercube accommodates up to 8 ($2^{d=3}$) mappings. If there are fewer than $2^d$ codes in the global set, then not all vertices in the hypercube will be mapped and some vertices may be left unused.

Referring to FIGS. 3A through 3F, subsets A through F of the global set may be represented based on the application of Boolean logic operations (e.g., a conjunction clause) to the Boolean literals representing each code. As provided in further detail below, the result of the operations applied to the Boolean literals can be interpreted as hyper-rectangles that form a cross-section of the d-dimensional hypercube representing each subset A through F in the exemplary figures.

Accordingly, a mapping range using k Boolean literals in a d-dimensional hypercube represents a cross-section of up to a total of $2^{(d-k)}$ codes. For example, in FIG. 3C, two such ranges are defined. The first range defined by a Boolean clause '**0' has k=1 literal and may be represented by the square covering the $2^{23-1=2}$=4 codes {2,5,3,6}. The second range defined by a Boolean clause '10*', for example, has k=2 literals and is the line covering the $2^{23-2=1}$=2 codes {3,7}. In these examples, a '*' is a wildcard character indicating that the Boolean literal may be either 1 or 0.

In one embodiment, a Boolean clause that represents a subset of the global code set may be represented as a data structure such as a lookup table. In a first implementation (I), the lookup table may include two d-bit words, where the bits in the first word identify the Boolean literals that are present in a Boolean clause, and the bits in the second word indicate the respective values of the bits that are present in the Boolean clause.

For example, Boolean clause '**0' may be represented by two 3-bit words: 001 and 000

First word '001'—The two leading zeros indicate that the two leading values in the Boolean clause can be either 0 or 1. The last bit that is set to 1 indicates that the value of the last bit in the Boolean clause is equal to the value of the last bit in the second word.

Second word '000'—Since the first two leading bits in the Boolean clause can be either 0 or 1, the values of the first two bits in this word are unimportant. For simplicity in the examples provided here, a value of 0 is assigned to bits in the second word that are designated as * in the Boolean clause (i.e., the second word can be either of '000', '010', '100', '110'). The last bit gives the value of the final bit in the Boolean clause, since the last bit in the first word was 1).

Figure 3A:
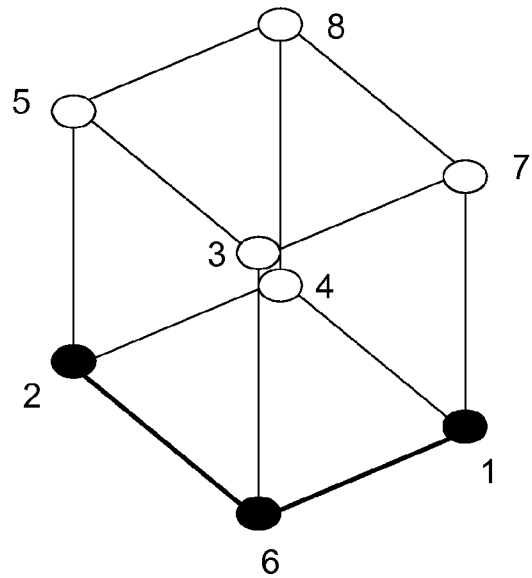
FIGS. 3A to 3F are exemplary scenarios for representing the subsets of the global code set of FIG. 1 as a cross-section of the multi-dimensional data structure in accordance with one embodiment.
Figure 3B:
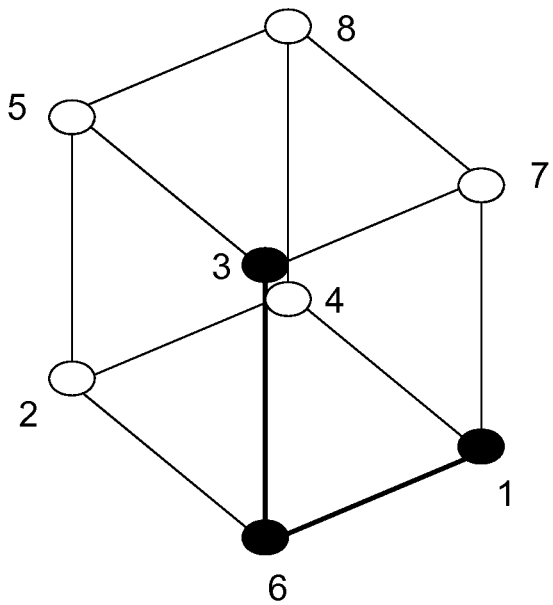
Figure 3C:
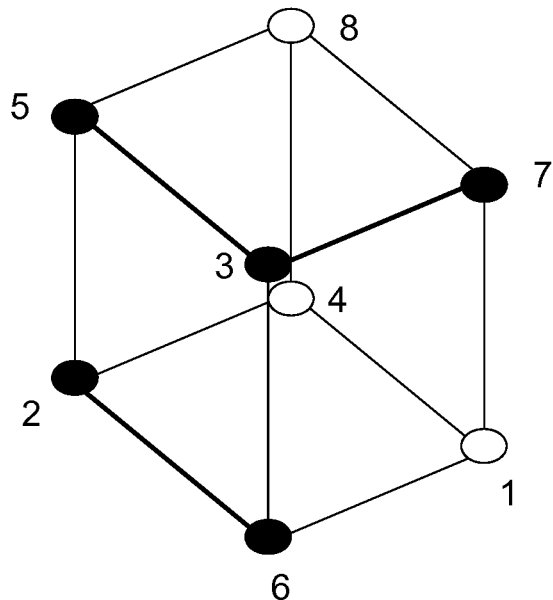
Figure 3D:
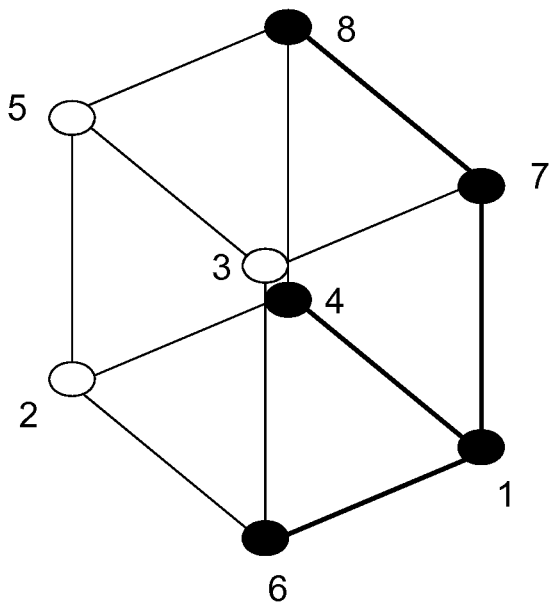
Figure 3E:
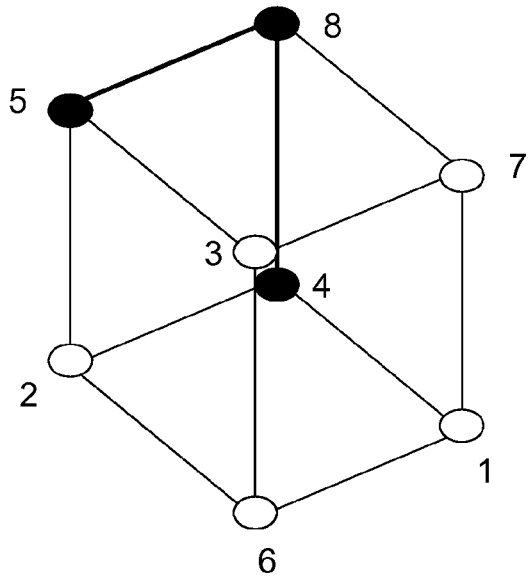
Figure 3F:
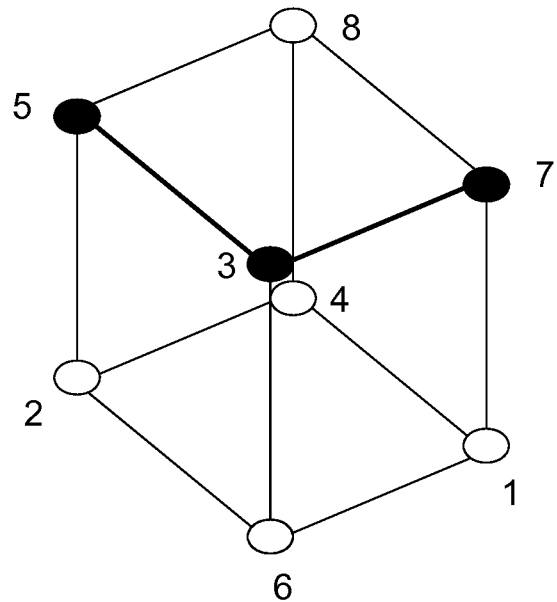

Referring to FIG. 3C, for example, codes 2, 3, 5, 6, 7 are members of Set C={2,3,5,6,7} as represented by shaded nodes in the hypercube. The Boolean literals associated with codes 2, 3, 5, 6, 7 are '010', '100', '110', '000' and '101' respectively. As such, set C may be represented by the assignment C=(0*0 or 00*). Thus, by way of example, Boolean clauses for set C may be represented as provided below, according to the first implementation (I) above:

**0→001 000[first word=001; second word=000]

10*→110 100 [first word=110; second word=100]

In this example first implementation (I), an alternate representation for set C may be:

**0→001 000[first word=001; second word=000]

101→111 101[first word=111; second word=101]

In a second implementation (II), the lookup table may include a one-bit word to indicate whether the clause uses the maximum of d Boolean literals. If so, the one-bit word is followed by a d-bit word with the values of said Boolean literals. Otherwise, the one-bit word is followed by two d-bit words as in the first implementation (I).

Referring again to FIG. 3C, by way of example, Boolean clauses for set C may be represented as provided below, according to the second implementation (II):

**0→0 001 000

10*→0 110 100

In this example second implementation (II), an alternate representation for set C may be:

**0→0 001 000

101→1 101

In the second implementation (II), as illustrated above, the indicator bit, when set to 0, indicates that 2 d-bit words follow (similar to the first implementation). Otherwise, the bit is set to 1 to indicate that all d Boolean literals are specified in the word to follow where values for all literals are provided (see the last line of the alternate representation above).

In one embodiment, to determine whether a code falls in a subset of the global code set, the target code is converted into its mapped points in the hypercube and then a test is applied to the assignment clause defined for a subset to determined if the target code is in that subset.

Referring to the above examples for FIG. 3C, the assignment clause C for set C under the first implementation (I) is represented as:

C=**0 or 10* where

**0→001 000 [y1=001; z1=000]

10*→110 100 [y2=110; z2=100]

In one embodiment, the test to determine whether a code x is in the set represented by a Boolean literal as yz (where y is the first word and z is the second word) is to determine whether ((x XOR z) AND y)=0. If so, then x is a member of the set. In other words:

For C=y1z1 or y1z2 or ... or $y_i z_i$ if $((x_i \text{ XOR } z_i) \text{ AND } y_i)=0$ then a code $x_i$ is in set C, where $x_i$ represents the target code, and $y_i$ and $z_i$ represent the first and second words of the respective Boolean clauses that define set C.

As an example, if we test for codes x1=110 and x2=001, we have:

(x1 XOR 000) AND 001=000 (match)

(x2 XOR 000) AND 001=001 (no match)

(x2 XOR 100) AND 110=100 (no match)

Thus, the test results indicate that code x1 is included in set C, but code x2 is not.

In case of the clause representation in the second implementation (II) above, if the clause has less than d literals, the test is the same as above. Otherwise, let z be the second word indicating the values of set variables (of which there are exactly d). Then x matches the clause (i.e., is in the set represented by the clause) if x=z. Thus, if set C is represented as follows:

**0→0 001 000

101→1 101

Then for x1 the same calculation applies (since x1 matches the clause **0). For x2, when testing against the second clause, the test is made directly:

x2=101?(no match)

Thus, the test results provides similar results indicating that code x1 is included in set C, but code x2 is not.

It is noteworthy that the traditional test for determining whether a code x is in a range defined as [a,b], for example, is based on the following: a<=x && x<=b, where a<=x and x<=b. Calculation of each clause uses one arithmetic operation and 1 flag check. Therefore, it is 2 arithmetic operations and 2 flag checks (or, depending on implementation, 3 arithmetic operations and 1 flag check).

In accordance with one embodiment, [a,b] is stored as [a,b-a] (i.e., a range starting at "a", of length "b-a"). In this embodiment, the test is performed using unsigned arithmetic as x-a<=b-a which takes 2 arithmetic operations and 1 flag check. For a system which differentiates between single codes and ranges (of size greater than 1), a bit would be needed to indicate this difference. Thus, for a single code, 1 arithmetic operation and 2 flag checks are needed. For a range check, 2 arithmetic operations and 2 flag checks are needed at the very least.

For the first implementation (I) above, there are 2 arithmetic operations and 1 flag check. For the second implementation (II), where the system differentiates between single codes and ranges (of size greater than 1), 1 arithmetic operation and 2 flag checks are needed for a single code, and 2 arithmetic operations and 2 flag checks are needed for a range check. Thus, the two implementations disclosed here are at least as efficient as the tradition approach which uses one-dimensional ranges.

The disclosed embodiments here may be substantially more efficient if the traditional approach didn't map non-integer codes to integers, in which case much more expensive equality or bounds checking may be needed. Intermediate numbers of dimensions (i.e., less than d) hinder performance, since each dimension needs to be checked separately. This can be illustrated via a 2-dimensional representation, where a range may be represented as [(a,b), (e,f)] and the mapped point as (x,y).

In the above, the mapped point is included if a<=x && x<=b && e<=y && y<=f. This is a more expensive test, requiring at least twice the number of operations. Increasing dimensions makes the test even more expensive as each (non-binary) dimension is range-tested separately. However, using the d-dimensional representation used above, the dimensions may be tested simultaneously.

Give the above representation, a table of codes (i.e., a set of codes) may be represented by the OR between AND clauses (i.e., as a disjunctive normal form (DNF)). The clauses for vertices which aren't mapped to or from any code may be included in a "don't care" DNF. Given this information we can generate a minimal DNF for the table by using logic minimization techniques (the "don't care" DNF is relevant, since the outcome may be minimized by covering some of the "don't care" vertices. This doesn't affect semantics since an unmapped vertex may not be tested for inclusion).

The above implementation may be further extended to generate a minimal table "graph" using logic minimization techniques (e.g., a minimal sum of sum of products for representing "table-of-codes" DNFs, given those DNFs and the "don't care" DNF). Thus, not only do we have a range representation that is amenable to efficient code-matching computations, we also have the mechanism needed to generate the range instances so as to create compact tables. This approach does not worsen the table sizes, and will likely reduce them significantly.

In the following, two algorithms for implementing the mapping are provided. We note that it is likely that "good" mappings exist (i.e., which reduces the size of the DNF representation significantly). This is because each vertex of the d-dimensional hyper-cube has d neighbors, and may be included in up to 2d−1 different AND clauses, providing flexibility which the mapping algorithm may utilize.

The first algorithm is a genetic algorithm which tries to globally optimize the result. A genetic algorithm is a search heuristic that mimics the process of natural evolution. The codes are assigned to a random permutation of the numbers 0 . . . n−1 for each member of the population. A fitness function may be defined by performing the logic minimization (over the binary representation of the numbers) and determining the size of the output, or by processing the permutation to generate some relevant heuristic or approximation of the value (e.g., the total number of tables shared by immediate neighbors).

The second algorithm works by gradually building up the mapping, bottom up, like a binary tree, for example. At the start of iteration $j=0, 1, \ldots$, there are $n/2^j$ j-dimensional hyper-cubes. During each iteration, the hyper-cubes are combined in pairs to create the hyper-cubes for the next iteration. The mapping is created efficiently (in time $O(n^2(\log n+S))$ and space $O(n^2)$ where n is the number of codes and S is the number of input sets) in a greedy manner in order to try and minimize the total number of clauses (summed over all the sets) before DNF minimization.

In one embodiment, input to the system is a group of sets over the codes. A code is associated with a specific node. The node may be connected to other nodes. A code is associated with a point (whose dimension grows from iteration to iteration). The point has a value of +/−1 in each dimension during construction, and a value of 0 or 1 in each dimension after construction. A cube is a data structure storing various nodes. The size of a cube is the number of nodes stored in it. For a code x its associated node, point and cube are Nx, Px, and Cx, respectively.

In one implementation, a pair includes two codes (x,y) and is unordered, in that the order of (x,y) or (y,x) is immaterial. A data structure is used to map a code to its cube. The data structure includes the current cube (which starts as empty). An ordered data structure, O, is used for storing pairs of codes. Pairs of codes included in the data structure O are preferably ordered by decreasing co-occurrence count. Thus, for each code x, a data structure Ox is implemented to store pairs (x,y), ordered by decreasing co-occurrence count, for example.

An example algorithm for initializing and constructing the data structure Ox is provided below:

Initialization phase:
  For each code x:
  Create a node Nx with an empty label
  Create a cube Cx containing Nx. Map x to Cx. Store Cx
  Create Ox
  Count the number of sets in which each pair (x,y) of codes co-occurs, and insert the pair to Ox and Oy Construction phase:
  While # of cubes >1:
    For each code x, let (x, tx) be the pair with the highest co-occurrence count in Ox. Insert (x,tx) into O
    C=used codes for this iteration (starts empty)
    While O isn't empty:
      Remove the pair (x,y) with the highest co-occurrence count from O
      If x is in C or y is in C, continue
      Remove x's cube, Cx and y's cube Cy.
      Create a new cube, Cnew for the "connection" of Cx to Cy and store.
      Create a system of linear equations, where a matrix A, of size $(\log |Cx|)*(\log|Cx|)$ represents the permutation and reflection matrix (i.e. in each row and column A has a single non-zero value which may be +/−1) which "specifies" how the points in Cy are to be "transformed" so that each point matches its future neighboring point from Cx in the first $\log|Cx|$ dimensions:
      Add the constraint that A*Py=Px
      Create sets Sx and Sy
      While the number of constraints <log|Cx|

Find the pair (u,v) such that Nu is a neighbor of Nx which isn't in Sx and Nv is a neighbor of Ny which isn't in Sy with the highest co-occurrence count
Add the constraint that A*Pv=Pu
Add u to Sx
Add v to Sy
Solve the system of linear equations (resulting in A being precisely defined—this can be done in time |A|)
For all u in Cx
Add u to C
Map u to Cnew
Increase Pu's dimension:
Set Pu=−1,Pu
For all v in Cy
Add v to C
Map v to Cnew
Increase Pv's dimension:
Set Pv=1,A*Pv
For all pairs (u,v) such that u is in Cx and v is in Cy:
Remove the pair (u,v) from Ou and Ov.
If Pu XOR Pv=100 . . . 0 connect Nu to Nv
If |C|!=V (there is an extra cube left over) for x not in C
Increase Px's dimension: set Px=−1,Px
Completion phase:
For every x set Px=(Px+1)/2

In different embodiments, the claimed subject matter may be implemented as a combination of both hardware and software elements, or alternatively either entirely in the form of hardware or entirely in the form of software. Further, computing systems and program software disclosed herein may comprise a controlled computing environment that may be presented in terms of hardware components or logic code executed to perform methods and processes that achieve the results contemplated herein. Said methods and processes, when performed by a general purpose computing system or machine, convert the general purpose machine to a specific purpose machine.

Figure 4A:
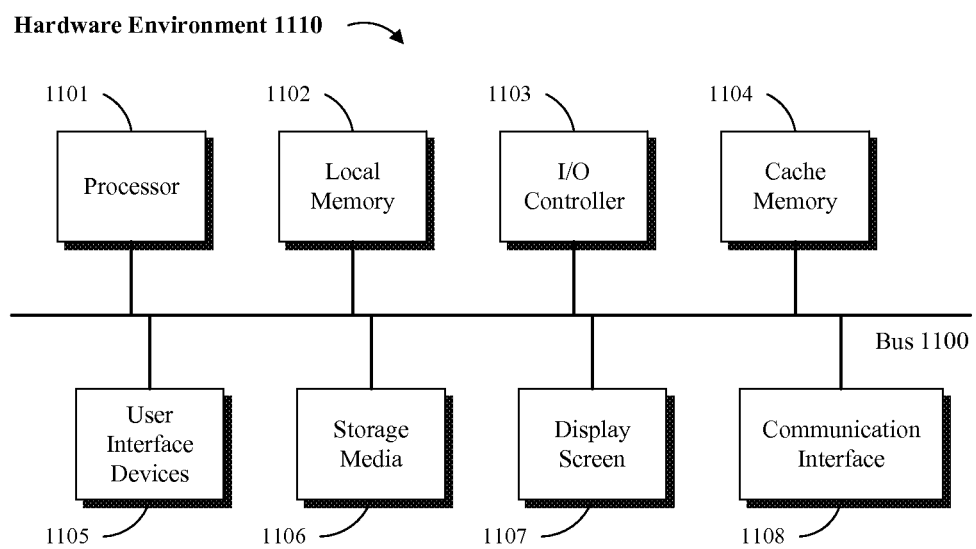
FIGS. 4A and 4B are block diagrams of hardware and software environments in which the disclosed systems and methods may operate, in accordance with one or more embodiments.
Figure 4B:
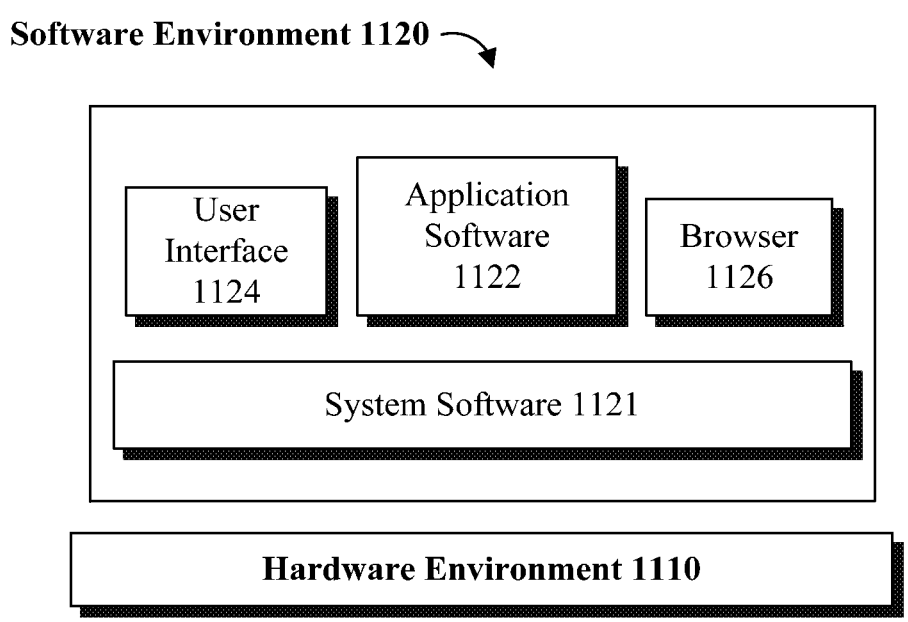

Referring to FIGS. 4A and 4B, a computing system environment in accordance with an exemplary embodiment may be composed of a hardware environment 1110 and a software environment 1120. The hardware environment 1110 may comprise logic units, circuits or other machinery and equipments that provide an execution environment for the components of software environment 1120. In turn, the software environment 1120 may provide the execution instructions, including the underlying operational settings and configurations, for the various components of hardware environment 1110.

Referring to FIG. 4A, the application software and logic code disclosed herein may be implemented in the form of computer readable code executed over one or more computing systems represented by the exemplary hardware environment 1110. As illustrated, hardware environment 110 may comprise a processor 1101 coupled to one or more storage elements by way of a system bus 1100. The storage elements, for example, may comprise local memory 1102, storage media 1106, cache memory 1104 or other computer-usable or computer readable media. Within the context of this disclosure, a computer usable or computer readable storage medium may include any recordable article that may be utilized to contain, store, communicate, propagate or transport program code.

A computer readable storage medium may be an electronic, magnetic, optical, electromagnetic, infrared, or semiconductor medium, system, apparatus or device. The computer readable storage medium may also be implemented in a propagation medium, without limitation, to the extent that such implementation is deemed statutory subject matter. Examples of a computer readable storage medium may include a semiconductor or solid-state memory, magnetic tape, a removable computer diskette, a random access memory (RAM), a read-only memory (ROM), a rigid magnetic disk, an optical disk, or a carrier wave, where appropriate. Current examples of optical disks include compact disk, read only memory (CD-ROM), compact disk read/write (CD-R/W), digital video disk (DVD), high definition video disk (HD-DVD) or Blue-ray™ disk.

In one embodiment, processor 1101 loads executable code from storage media 1106 to local memory 1102. Cache memory 1104 optimizes processing time by providing temporary storage that helps reduce the number of times code is loaded for execution. One or more user interface devices 1105 (e.g., keyboard, pointing device, etc.) and a display screen 1107 may be coupled to the other elements in the hardware environment 1110 either directly or through an intervening I/O controller 1103, for example. A communication interface unit 1108, such as a network adapter, may be provided to enable the hardware environment 1110 to communicate with local or remotely located computing systems, printers and storage devices via intervening private or public networks (e.g., the Internet). Wired or wireless modems and Ethernet cards are a few of the exemplary types of network adapters.

It is noteworthy that hardware environment 1110, in certain implementations, may not include some or all the above components, or may comprise additional components to provide supplemental functionality or utility. Depending on the contemplated use and configuration, hardware environment 1110 may be a desktop or a laptop computer, or other computing device optionally embodied in an embedded system such as a set-top box, a personal digital assistant (PDA), a personal media player, a mobile communication unit (e.g., a wireless phone), or other similar hardware platforms that have information processing or data storage capabilities.

In some embodiments, communication interface 1108 acts as a data communication port to provide means of communication with one or more computing systems by sending and receiving digital, electrical, electromagnetic or optical signals that carry analog or digital data streams representing various types of information, including program code. The communication may be established by way of a local or a remote network, or alternatively by way of transmission over the air or other medium, including without limitation propagation over a carrier wave.

As provided here, the disclosed software elements that are executed on the illustrated hardware elements are defined according to logical or functional relationships that are exemplary in nature. It should be noted, however, that the respective methods that are implemented by way of said exemplary software elements may be also encoded in said hardware elements by way of configured and programmed processors, application specific integrated circuits (ASICs), field programmable gate arrays (FPGAs) and digital signal processors (DSPs), for example.

Referring to FIG. 4B, software environment 1120 may be generally divided into two classes comprising system software 1121 and application software 1122 as executed on one or more hardware environments 1110. In one embodiment, the methods and processes disclosed here may be implemented as system software 1121, application software 1122, or a combination thereof. System software 1121 may comprise control programs, such as an operating system (OS) or an information management system, that instruct one or more processors 1101 (e.g., microcontrollers) in the hardware environment 1110 on how to function and process information. Application software 1122 may comprise but is not limited to program code, data structures, firmware, resident software, microcode or any other form of information or routine that may be read, analyzed or executed by a processor 1101.

In other words, application software 1122 may be implemented as program code embedded in a computer program product in form of a computer-usable or computer readable storage medium that provides program code for use by, or in connection with, a computer or any instruction execution system. Moreover, application software 1122 may comprise one or more computer programs that are executed on top of system software 1121 after being loaded from storage media 1106 into local memory 1102. In a client-server architecture, application software 1122 may comprise client software and server software. For example, in one embodiment, client software may be executed on a client computing system that is distinct and separable from a server computing system on which server software is executed.

Software environment 1120 may also comprise browser software 1126 for accessing data available over local or remote computing networks. Further, software environment 1120 may comprise a user interface 1124 (e.g., a graphical user interface (GUI)) for receiving user commands and data. It is worthy to repeat that the hardware and software architectures and environments described above are for purposes of example. As such, one or more embodiments may be implemented over any type of system architecture, functional or logical platform or processing environment.

It should also be understood that the logic code, programs, modules, processes, methods and the order in which the respective processes of each method are performed are purely exemplary. Depending on implementation, the processes or any underlying sub-processes and methods may be performed in any order or concurrently, unless indicated otherwise in the present disclosure. Further, unless stated otherwise with specificity, the definition of logic code within the context of this disclosure is not related or limited to any particular programming language, and may comprise one or more modules that may be executed on one or more processors in distributed, non-distributed, single or multiprocessing environments.

As will be appreciated by one skilled in the art, a software embodiment may include firmware, resident software, microcode, etc. Certain components including software or hardware or combining software and hardware aspects may generally be referred to herein as a "circuit," "module" or "system." Furthermore, the subject matter disclosed may be implemented as a computer program product embodied in one or more computer readable storage medium(s) having computer readable program code embodied thereon. Any combination of one or more computer readable storage medium(s) may be utilized. The computer readable storage medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing.

In the context of this document, a computer readable storage medium may be any tangible medium that can contain, or store a program for use by or in connection with an instruction execution system, apparatus, or device. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable storage medium may be transmitted using any appropriate medium, including but not limited to wireless, wireline, optical fiber cable, RF, etc., or any suitable combination of the foregoing. Computer program code for carrying out the disclosed operations may be written in any combination of one or more programming languages, including an object oriented programming language such as Java, Smalltalk, C++ or the like and conventional procedural programming languages, such as the "C" programming language or similar programming languages.

The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Certain embodiments are disclosed with reference to flowchart illustrations and/or block diagrams of methods, apparatus (systems) and computer program products according to embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable storage medium that can direct a computer, other programmable data processing apparatus, or other devices to function in a particular manner, such that the instructions stored in the computer readable storage medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures.

For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The claimed subject matter has been provided here with reference to one or more features or embodiments. Those skilled in the art will recognize and appreciate that, despite of the detailed nature of the exemplary embodiments provided here, changes and modifications may be applied to said embodiments without limiting or departing from the generally intended scope. These and various other adaptations and combinations of the embodiments provided here are within the scope of the disclosed subject matter as defined by the claims and their full set of equivalents.

What is claimed is:

1. A computer implemented method for verifying membership in one or more sets that are subsets of a global set, the method comprising:
   representing members of the global set by mapping each member to a distinct Boolean variable of length d, wherein $2^d$ is not less than the number of members in the global set;
   representing a subset of the global set by a Boolean expression which evaluates to a first value for any of the assignments to the Boolean variables which represent members of the subset, and which evaluates to a second value for any of the assignments to the Boolean variables which represent members of the global set that are not members of the subset, wherein the Boolean expression is constructed from one or more subsets so as to be evaluated efficiently for any assignment to the Boolean variables which represent members of the global set; and
   determining membership of a target member of the global set in a target subset of the global set by evaluating the Boolean expression that represents the target subset based on the mapping of the target member;
   wherein the Boolean expressions representing the subsets C of the global set are in disjunctive normal form (DNF) or conjunctive normal form (CNF)
wherein the Boolean expression is represented by pairs of words $y_1 z_1, y_1 z_2, \ldots, y_k z_k$, wherein $y_i$ and $z_i$ represent a first word and a second word of length d-bits or greater and are used to represent the $i^{th}$ clause in the Boolean expression; the $j^{th}$ bit in $y_i$ is 1 when the $j^{th}$ Boolean variable is present in the clause and 0 when it is not present; when it is present, then:
   when the Boolean expression is in DNF: the $j^{th}$ bit in $z_i$ is 1 if the $i^{th}$ Boolean variable is true and 0 otherwise; and
   when the Boolean expression is in CNF: the $j^{th}$ bit in $z_i$ is 0 if the $i^{th}$ Boolean variable is true and 1 otherwise;
   wherein said representing members of the global set by mapping, said representing a subset of the global set by a Boolean expression, and said determining membership configured by a computing unit programmed to carry out perform the steps of the method using a processor; and wherein a member of the global set, g, represented by a mapping $x_g$, is tested for membership in C, where:
DNF: g is a member of C if for any i between 1 and k:

$$((x_g \text{ XOR } z_i) \text{ AND } y_i) = 0;$$

CNF: g is not a member of C if for any i between 1 and k:

$$((x_g \text{ XOR } z_i) \text{ AND } y_i) = 0.$$

2. The method of claim 1, wherein the Boolean expressions representing the subsets of the global set are constructed using logic minimization techniques.

3. A system for verifying membership in one or more sets that are subsets of a global set, the system comprising:
   a processor;
   a first logic unit which uses said processor for representing members of the global set by mapping each member to a distinct Boolean variable of length d, wherein $2^d$ is not less than the number of members in the global set;
   a second logic unit which uses said processor for representing a subset of the global set by a Boolean expression which evaluates to a first value for any of the assignments to the Boolean variables which represent members of the subset, and which evaluates to a second value for any of the assignments to the Boolean variables which represent members of the global set that are not members of the subset, wherein the Boolean expression is constructed from one or more subsets so as to be evaluated efficiently for any assignment to the Boolean variables which represent members of the global set; and
   a third logic unit which uses said processor for determining membership of a target member of the global set in a target subset of the global set by evaluating the Boolean expression that represents the target subset based on the mapping of the target member wherein the Boolean expressions representing the subsets C of the global set are in disjunctive normal form (DNF) or conjunctive normal form (CNF);
wherein the Boolean expression is represented by pairs of words $y_1 z_1, y_1 z_2, \ldots, y_k z_k$, wherein $y_i$ and $z_i$ represent a first word and a second word of length d-bits or greater and are used to represent the clause in the Boolean expression; the $j^{th}$ bit in $y_i$ is 1 when the $j^{th}$ Boolean variable is present in the clause and 0 when it is not present; when it is present, then:
   when the Boolean expression is in DNF: the $j^{th}$ bit in $z_i$ is 1 if the $i^{th}$ Boolean variable is true and 0 otherwise; and
   when the Boolean expression is in CNF: the $j^{th}$ bit in $z_i$ is 0 if the $i^{th}$ Boolean variable is true and 1 otherwise; and
wherein a member of the global set, g, represented by a mapping $x_g$, is tested for membership in C, where:
DNF: g is a member of C if for any i between 1 and k:

$$((x_g \text{ XOR } z_i) \text{ AND } y_i) = 0;$$

CNF: g is not a member of C if for any i between 1 and k:

$$((x_g \text{ XOR } z_i) \text{ AND } y_i) = 0.$$

4. The system of claim 3, wherein the Boolean expressions representing the subsets of the global set are constructed using logic minimization techniques.

5. A computer program product comprising a non transitory computer readable storage medium having a computer readable program, wherein the computer readable program when executed on a computer causes the computer to:
   represent members of a global set by mapping each member to a distinct Boolean variable of length d, wherein $2^d$ is not less than the number of members in the global set;

represent a subset of the global set by a Boolean expression which evaluates to a first value for any of the assignments to the Boolean variables which represent members of the subset, and which evaluates to a second value for any of the assignments to the Boolean variables which represent members of the global set that are not members of the subset, wherein the Boolean expression is constructed from one or more subsets so as to be evaluated efficiently for any assignment to the Boolean variables which represent members of the global set; and determine membership of a target member of the global set in a target subset of the global set by evaluating the Boolean expression that represents the target subset based on the mapping of the target member;

wherein the Boolean expressions representing the subsets C of the global set are in disjunctive normal form (DNF) or conjunctive normal form (CNF);

wherein the Boolean expression is represented by pairs of words $y_1z_1, y_1z_2, \ldots, y_kz_k$, wherein $y_i$ and $z_i$ respectively represent a first word and a second word of length d-bits or greater and are used to represent the clause in the Boolean expression; the $j^{th}$ bit in $y_i$ is 1 when the $j^{th}$ Boolean variable is present in the clause and 0 when it is not present; when it is present, then:

when the Boolean expression is in DNF: the $j^{th}$ bit in $z_i$ is 1 if the $i^{th}$ Boolean variable is true and 0 otherwise; and when the Boolean expression is in CNF: the $j^{th}$ bit in $z_i$ is 0 if the $i^{th}$ Boolean variable is true and 1 otherwise; and wherein a member of the global set, g, represented by a mapping $x_g$, is tested for membership in C, where:

DNF: g is a member of C if for any i between 1 and k:

$((x_g \text{ XOR } z_i) \text{ AND } y_i)=0;$

CNF: g is not a member of C if for any i between 1 and k:

$((x_g \text{ XOR } z_i) \text{ AND } y_i)=0.$

6. The computer program product of claim 5, wherein the Boolean expressions representing the subsets of the global set are constructed using logic minimization techniques.

* * * * *